(12) United States Patent
Yanagawa et al.

(10) Patent No.: US 11,499,959 B2
(45) Date of Patent: Nov. 15, 2022

(54) NANOPORE-FORMING METHOD, NANOPORE-FORMING DEVICE AND BIOMOLECULE MEASUREMENT DEVICE

(71) Applicant: HITACHI HIGH-TECHNOLOGIES CORPORATION, Tokyo (JP)

(72) Inventors: Yoshimitsu Yanagawa, Tokyo (JP); Kenichi Takeda, Tokyo (JP); Itaru Yanagi, Tokyo (JP); Yusuke Goto, Tokyo (JP); Kazuma Matsui, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 846 days.

(21) Appl. No.: 16/463,502

(22) PCT Filed: Dec. 9, 2016

(86) PCT No.: PCT/JP2016/086812
§ 371 (c)(1),
(2) Date: May 23, 2019

(87) PCT Pub. No.: WO2018/105123
PCT Pub. Date: Jun. 14, 2018

(65) Prior Publication Data
US 2019/0369080 A1 Dec. 5, 2019

(51) Int. Cl.
*G01N 33/487* (2006.01)
*B01J 19/08* (2006.01)
(Continued)

(52) U.S. Cl.
CPC ........ *G01N 33/48721* (2013.01); *B01J 19/08* (2013.01); *B81C 1/00087* (2013.01);
(Continued)

(58) Field of Classification Search
CPC ................................. G01N 33/48721
See application file for complete search history.

(56) References Cited

U.S. PATENT DOCUMENTS

2015/0108008 A1 4/2015 Kwok et al.
2015/0109008 A1 4/2015 Godin et al.
2016/0162634 A1 6/2016 Reid et al.

FOREIGN PATENT DOCUMENTS

GB 2538482 A 11/2016
JP 2014-531901 A 12/2014
(Continued)

OTHER PUBLICATIONS

Cuifeng Ying, et al., "3d nanopore shape control by current-stimulus dielectric breakdown", Applied Physics Letters, 109, 063105(2016).
(Continued)

*Primary Examiner* — Nicholas A Smith
(74) *Attorney, Agent, or Firm* — Mattingly & Malur, PC

(57) ABSTRACT

A first modulation voltage is applied to a thin film. An amount of a change in the phase of a current carried through the thin film with respect to the phase of the first modulation voltage is compared with a threshold. Upon detecting that the amount of the change in the phase exceeds the threshold is detected, the application of the first modulation voltage is stopped. Thus, a nanopore is formed on the thin film at high speed.

15 Claims, 18 Drawing Sheets

(51) Int. Cl.
*C25F 3/12* (2006.01)
*B81C 1/00* (2006.01)
*G01N 33/00* (2006.01)
B23H 7/20 (2006.01)

(52) U.S. Cl.
CPC .................. *C25F 3/12* (2013.01); *B23H 7/20* (2013.01); *B81B 2201/0214* (2013.01); *B81B 2203/0127* (2013.01); *B81B 2203/0353* (2013.01); *G01N 2033/0095* (2013.01)

(56) References Cited

FOREIGN PATENT DOCUMENTS

| | | | |
|---|---|---|---|
| JP | 2015-517401 A | 6/2015 | |
| JP | 2015-525114 A | 9/2015 | |
| WO | 2015/152003 A1 | 10/2015 | |
| WO | WO-2017208631 A1 * | 12/2017 | .............. C12M 1/00 |

OTHER PUBLICATIONS

International Search Report of PCT/JP2016/086812 dated Mar. 14, 2017.

* cited by examiner

NANOPORE-FORMING METHOD, NANOPORE-FORMING DEVICE AND BIOMOLECULE MEASUREMENT DEVICE

TECHNICAL FIELD

The present invention relates to a nanopore forming method, a nanopore forming device, and a biomolecule measuring apparatus.

BACKGROUND ART

Nowadays, attention is focused on a biomolecule measuring apparatus using a nanometer-scale pore (in the following, referred to as a nanopore) formed on a thin film as a sensor. Patent Literature 1 and Nonpatent Literature 1 describe techniques in which a thin film formed with nanopores is disposed in an electrolytic solution, an ion current (a blockade current) carried through a nanopore is measured when a deoxyribonucleic acid (DNA) molecule passes through the inside of a nanopore, and hence the type of base is identified.

Compared with conventional DNA sequencers in accordance with fluorescence methods, the technique does not need any expensive fluorescent reagent, and does not need any DNA elongation reaction in sequencing. Thus, the technique is not prone to cause errors due to elongation reactions. Therefore, the technique is regarded as a promising new type of DNA sequencer that determines DNA base sequences at low costs with a high accuracy and long reads. The measurement target molecules are not only DNA but also ribonucleic acid (RNA), of course, and biopolymers, such as proteins, can also be evaluated with an appropriate selection of nanopore diameters, for example.

CITATION LIST

Patent Literature

Patent Literature 1: Japanese Unexamined Patent Application Publication (Translation of PCT Application) No. 2015-517401

Nonpatent Literature

Nonpatent Literature 1: Cuifeng Ying, et al., "3D nanopore shape control by current-stimulus dielectric breakdown", Applied Physics Letters, 109, 2016.

SUMMARY OF INVENTION

Technical Problem

DNA sequencers in accordance with nanopore methods can improve base encoding velocity (throughput) by the integration of nanopores and simultaneous measurement of blockade currents at the nanopores. However, the development history of nanopores is short. The alignment of nanopores is 500 nanopores at most as of 2015. This is far short of a few billions done by conventional DNA sequencers in accordance with fluorescence methods, and the throughput is slow by two digits or more. Therefore, it is expected that integration is further advanced in future and throughput is improved.

In the case in which nanopores are used in DNA sequencers, desirably, nanopores are formed immediately before sequencing. This is because nanometer-scale pores like nanopores easily change their shapes due to the natural oxidation of thin films or the attachment of organic substances, and nanopores are sometimes buried. Patent Literature 1 and Nonpatent Literature 1 disclose techniques in which a voltage or current stress is applied to a thin film to cause dielectric breakdown and hence nanopores are formed. In DNA sequencers in accordance with nanopore methods, from the viewpoint of the spatial resolution of the base, the thickness of the thin film is desirably thin, which is a thickness of a few nanometers or less, for example. Dielectric breakdown occurs at a voltage of about 10 V or less in such a thin film, and hence nanopores can be easily opened using a typical pulse generator. There is no need to use wide-scale facilities like a semiconductor processing system. Therefore, nanopores can be opened onsite immediately before sequencing.

In the pore forming method with voltage disclosed in Patent Literature 1, a high voltage that causes dielectric breakdown is applied to a thin film for a certain period of time, the voltage is then dropped to monitor a current, and hence the nanopore forming is detected. This is because the nanopore forming drops the electrical resistance of the thin film to carry a current. The reason why no current can be monitored with a high voltage being applied is that the application of a high voltage carries a tunnel current (a leakage current) through the thin film, and this causes no proper determination of the nanopore forming. Since the leakage current is exponentially more increased as the film thickness is thinner, in the application that the film thickness has to be a few nanometers like DNA sequencers specifically, the current has to be monitored with the voltage dropped.

In the case in which the current is monitored at a low voltage, a leakage current is kept carried for a while after the voltage is dropped. This is because it takes time to eliminate electric charges stored on the film. Thus, in the case in which the current is monitored as described above, the voltage is dropped and after a while, and then the current has to be measured. Such a waiting period might be acceptable when a single nanopore is formed. However, in the situations in which nanopores are arrayed in a large scale in future, it needs a long time to form nanopores one by one by the above-described method. Consequently, it can be thought that this causes a problem that it takes time to start DNA sequencing.

In view of the situation, the present invention is to provide a nanopore forming method that can accelerate the nanopore forming by performing an application of a nanopore forming voltage and monitoring of pore forming are performed in real time and that can start DNA sequencing at high speed even though an array scale is increased.

Solution to Problem

As an example, a nanopore forming method according to the present invention includes: applying a first modulation voltage to a thin film; comparing an amount of a change in a phase of a current carried through the thin film with respect to a phase of the first modulation voltage with a threshold; and upon detecting that the amount of the change in the phase exceeds the threshold, stopping application of the first modulation voltage.

As an example, a nanopore forming device according to the present invention includes: a power supply configured to apply a modulation voltage between a first electrode and a second electrode disposed such that the first electrode and the second electrode sandwich a chip including a thin film on which a nanopore is formed; a phase monitor configured to measure an amount of a change in a phase of a current carried between the first electrode and the second electrode on a phase of the modulation voltage; and a control circuit configured to stop application of the modulation voltage when the amount of the change in the phase of the current exceeds a threshold.

A biomolecule measuring apparatus according to the present invention includes: a nanopore device having a first chamber and a second chamber partitioned by a chip including a thin film, the first chamber and the second chamber being filled with an electrolytic solution, a first electrode disposed in the first chamber, and a second electrode disposed in the second chamber; a modulation voltage source configured to apply a modulation voltage for nanopore opening between the first electrode and the second electrode; a phase monitor configured to measure an amount of a change in a phase of a current carried between the first electrode and the second electrode with respect to a phase of the modulation voltage; a control circuit configured to stop application of the modulation voltage when the amount of the change in the phase of the current exceeds a threshold; a read voltage source configured to apply a read voltage for measuring a blockade current between the first electrode and the second electrode after a nanopore is formed on the thin film by application of the modulation voltage; and an information processor configured to identify a sequence of a biomolecule injected into the first chamber or the second chamber based on the blockade current carried through the nanopore when the read voltage is applied.

Advantageous Effects of Invention

According to the present invention, even though the integration degree of nanopores is increased, nanopores can be formed at high speed, and time until DNA sequencing is started can be shortened.

Problems, configurations, and effect other than those described above will be apparent from the description of embodiments below.

DESCRIPTION OF EMBODIMENTS

In the following, embodiments of the present invention will be described with reference to the drawings.

First Embodiment

Figure 1:
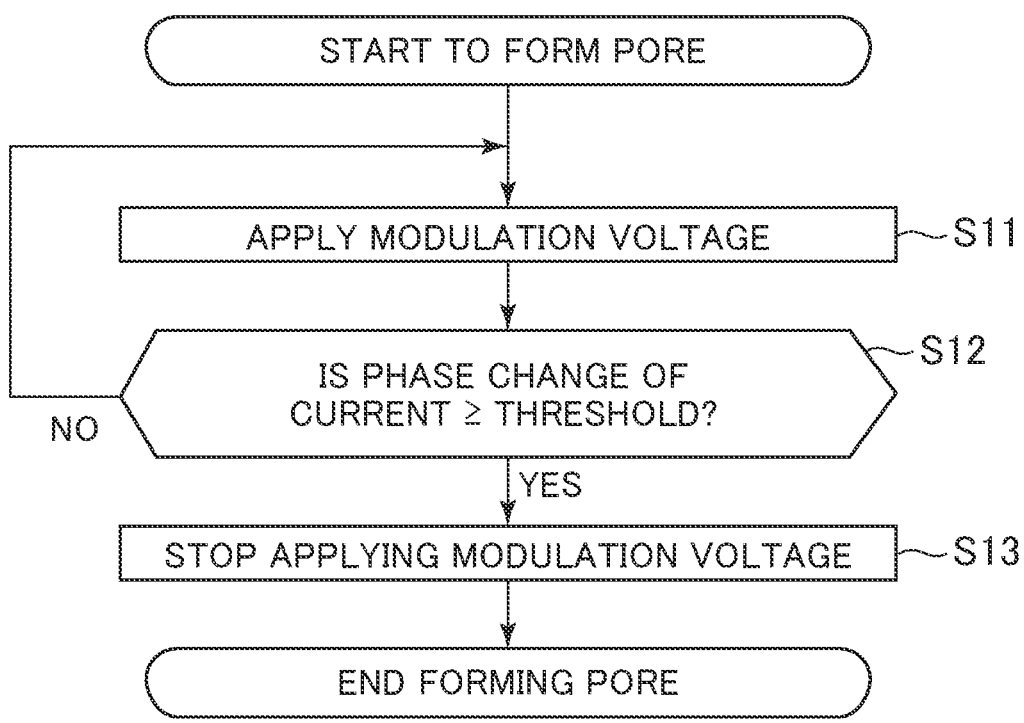
FIG. 1 is a flowchart of procedures of a nanopore forming method.

FIG. 1 is a flowchart of procedures of a nanopore forming method according to a first embodiment. The nanopore forming method according to the embodiment is as follows. After nanopore opening is started, a modulation voltage is applied to a thin film (S11). During the application of the modulation voltage, phase information on a current carried through the thin film is monitored. When an amount of change in a phase exceeds a predetermined threshold (S12), the application of the modulation voltage is stopped (S13), and nanopore opening is finished. The modulation voltage applied in Step S11 applies stress to the thin film, and a nanopore is formed by dielectric breakdown. The phase information on the current is always monitored, and hence nanopore forming can be detected real time. Stopping the application of the modulation voltage in Step S13 is stopping the modulation voltage for nanopore opening. After stopping the application, another modulation voltage that hardly contributes to nanopore opening may be applied. However, the amount of stress applied to the thin film has to be relatively smaller than the application voltage in nanopore opening. As long as this condition is satisfied, the voltage to be applied after stopping the application may be a DC voltage or a modulation voltage having another parameter.

Figure 2:
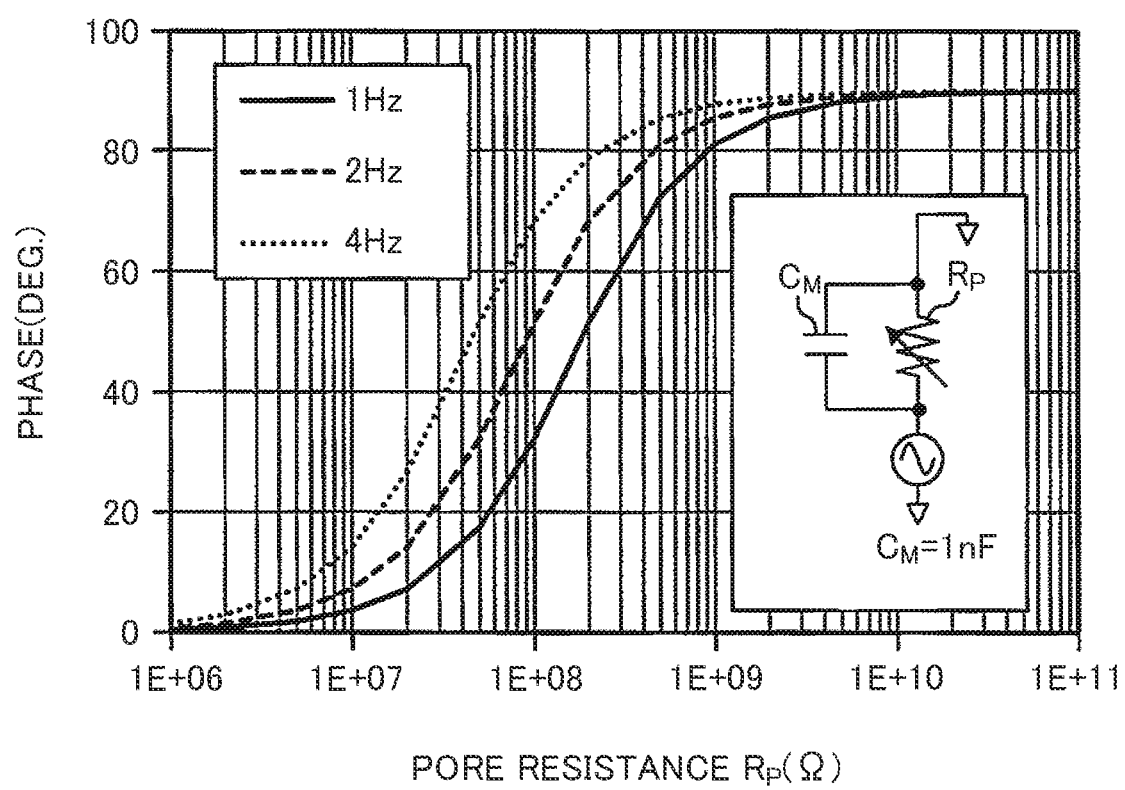
FIG. 2 is a diagram of an equivalent circuit of a thin film and a result that a change in a current phase corresponding to a change in a nanopore equivalent resistance is found by computing.

FIG. 2 is a diagram of an equivalent circuit of the thin film and a result that a change in a current phase corresponding to a change in a nanopore equivalent resistance is found by computing. Referring to FIG. 2, a phase change in the current due to forming of the nanopore will be described.

The thin film can be regarded as a circuit that a parasitic capacitance $C_M$ is mainly connected to a resistance $R_P$ of the nanopore in parallel. At this time, an impedance $Z_M$ of the thin film is expressed by Equations 1 and 2 below. A modulation method of the voltage applied to the thin film is non-limiting. However, here, a simple sine wave is assumed, which was $\sin(\omega t)$, where $\omega$ is an angular frequency. Equations 1 and 2 respectively express an absolute value component and a phase component of the impedance $Z_M$.

According to Equation 2, the phase of the current carried through the thin film goes by $\arctan(-\omega C_M R_P)$ with respect to the application voltage.

In FIG. 2, a pore resistance dependence of the phase of the current with respect to the phase of the application voltage is plotted as the frequency of the application voltage is a parameter based on Equation 2. Here, 1 nF is assumed as a capacitance of the thin film. The resistance value $R_P$ before the nanopore is formed is considerably, which is 10 GΩ or more, for example. Under this condition, since $C_M$ is dominant in the impedance of the thin film, the phase of the current goes by an angle of 90 degrees. After the application of the modulation voltage causes dielectric breakdown on the thin film and a pore is formed, the resistance value is dropped, and the advance of the phase of the current is slowed. For example, when the resistance of the formed nanopore is 1 GΩ and the modulation frequency is 1 Hz, the advance of the phase of the current is dropped to an angle of 80 degrees.

[Equation 1]

$$|Z_M| = \frac{R_P}{\sqrt{1 + \omega^2 C_M^2 R_P^2}} \quad (1)$$

[Equation 2]

$$\angle Z_M = \arctan(-\omega C_M R_P) \quad (2)$$

Figure 3:
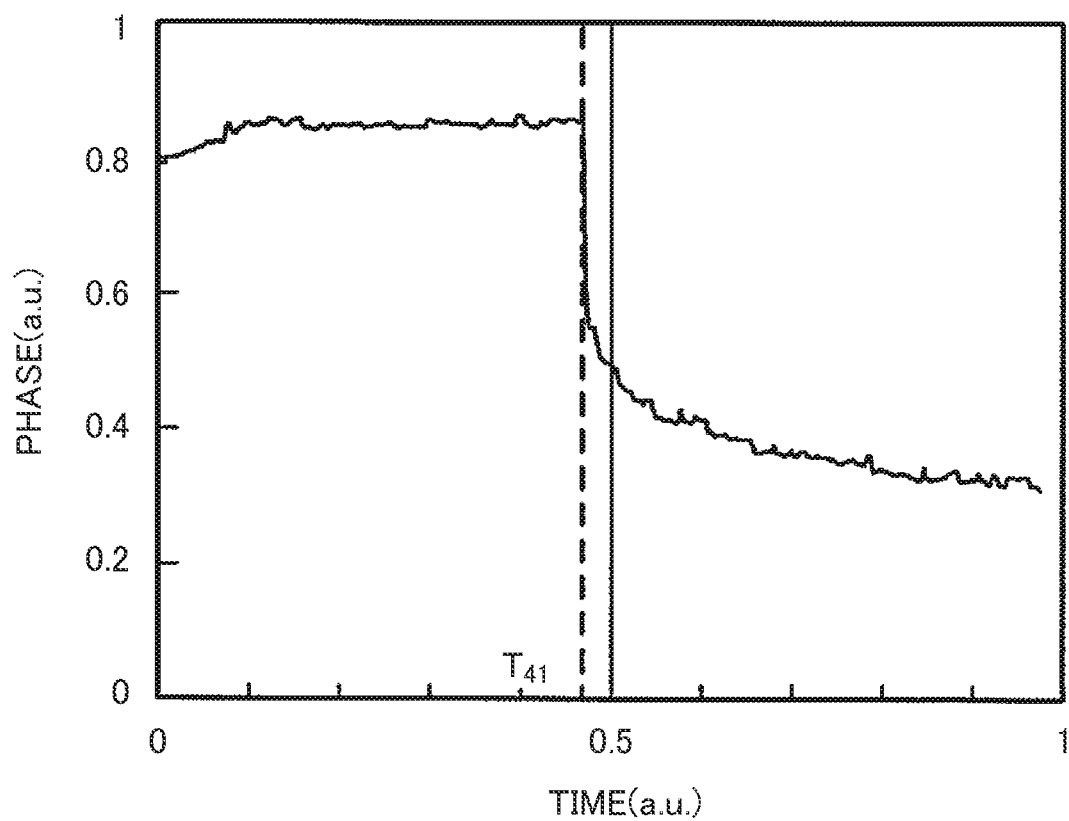
FIG. 3 is a diagram of a waveform actually measured showing a time variation in a phase of the current when a nanopore is formed on a thin film.

FIG. 3 is a graph plotting a time variation in the phase of the current when a sine wave voltage is applied to an SiN thin film in a thickness of 7 nm prototyped by semiconductor processes and a nanopore is formed. The vertical axis expresses the value that normalizes the phase of the current with respect to the application voltage where an angle of 100 is one. It is shown that the phase is almost constant from the beginning of the application of the voltage to at time $T_{41}$ which a nanopore is opened, the nanopore is opened at time $T_{41}$, and the advance of the phase is dropped. Monitoring this change in the phase enables the detection of the opening of the nanopore.

Figure 4:
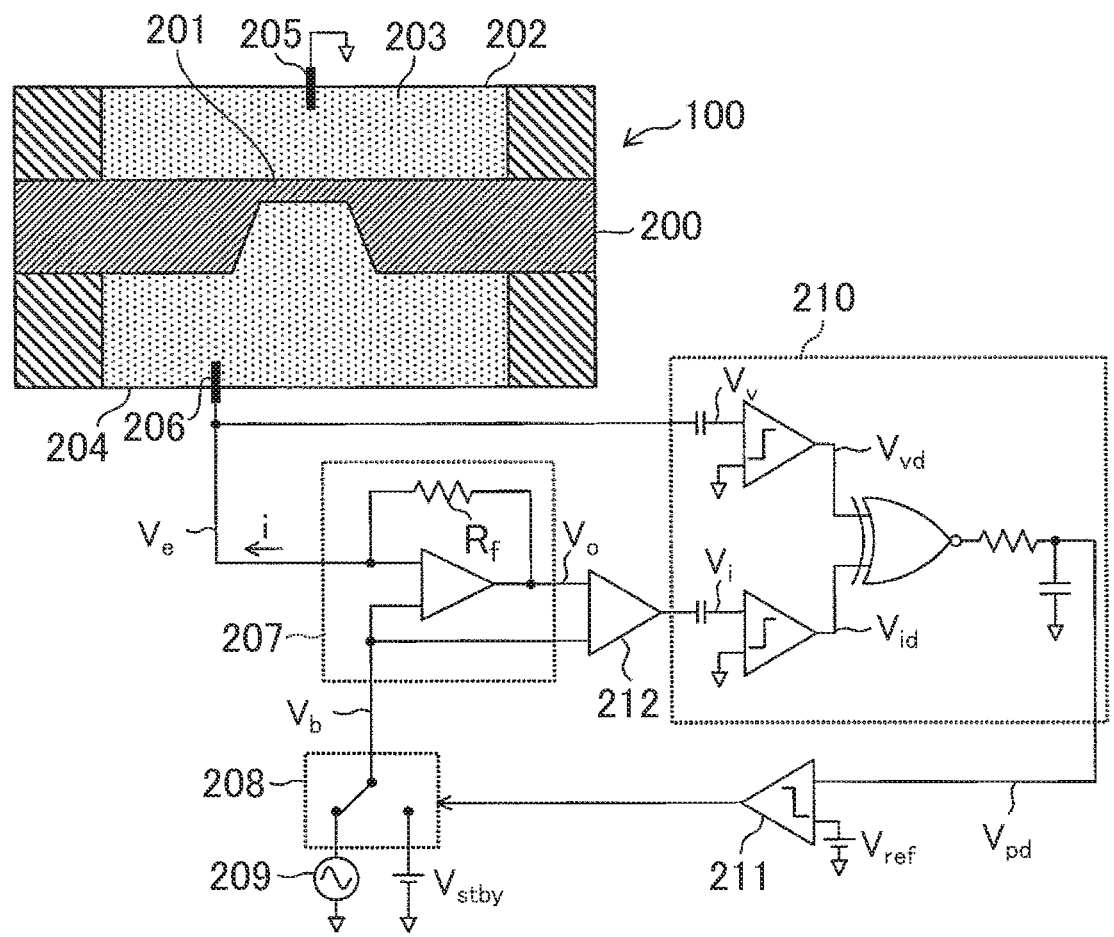
FIG. 4 is a circuit diagram of an exemplary configuration of a nanopore forming device.
Figure 5:
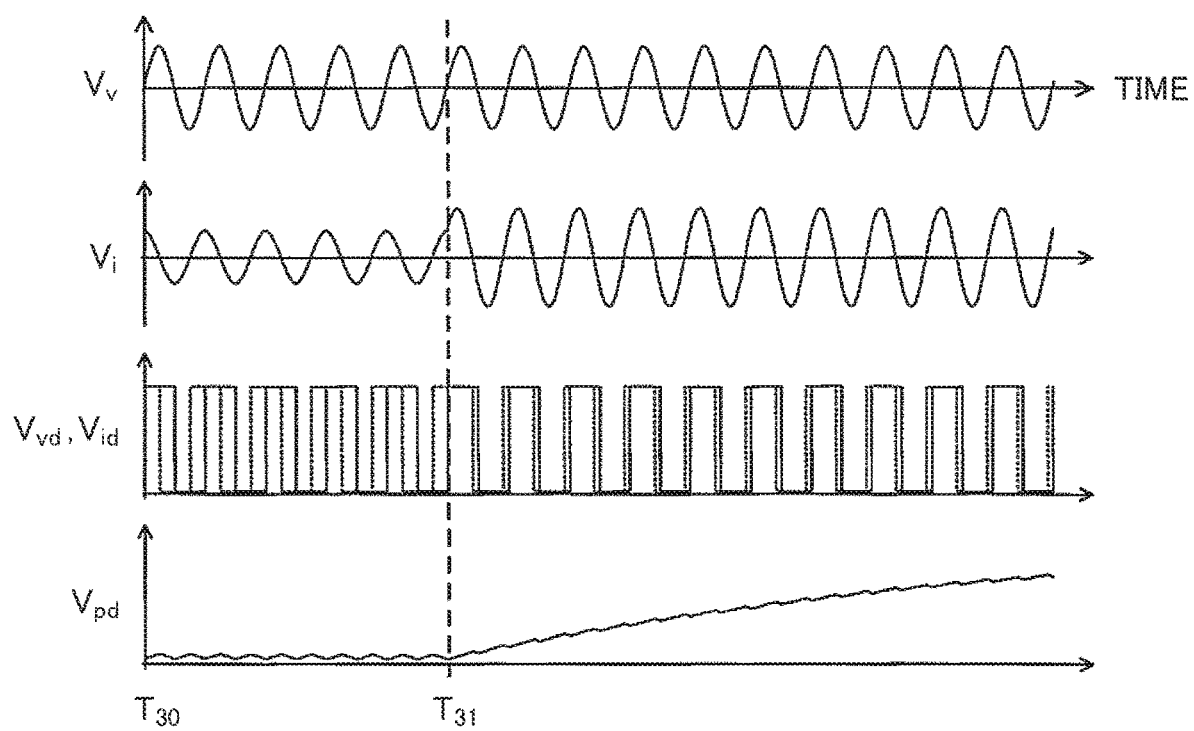
FIG. 5 is a diagram of an exemplary voltage waveform of a circuit.

FIG. 4 is a circuit diagram of an exemplary configuration of a nanopore forming device that implements the nanopore forming method according to the embodiment. FIG. 5 is a diagram of an exemplary voltage waveform of the circuit in FIG. 4. Referring to FIGS. 4 and 5, a specific exemplary configuration that implements the procedures in FIG. 1 will be described.

The nanopore forming device according to the embodiment has a modulation voltage source 209, a switch 208, a transimpedance amplifier 207, a phase monitor 210, and a comparator 211. The nanopore forming device is connected to a nanopore device 100 including a chip 200, a common chamber 202, and a first chamber 204 that is an individual chamber, and the nanopore forming device forms a nanopore on a thin film in the nanopore device 100. Each chambers of the nanopore device 100 is filled with an electrolytic solution 203. The chip 200 isolates the electrolytic solution in the common chamber 202 from the electrolytic solution in the first chamber 204. The common chamber 202 has a common electrode 205. The first chamber 204 has a first electrode 206 that is an individual electrode. The electrodes are immersed in the electrolytic solution 203. On the chip 200, a thin film 201 is formed. The thin film 201 is considerably thin, and has a thickness ranging from sub-nanometers to a few tens nanometers, for example, suitable for a biomolecular sample that is a measurement target. Such the thin film that is considerably thin can be formed by semiconductor processes. For example, a material of the chip 200 is silicon, and SiN (silicon nitride) is deposited on the chip 200, and hence such the thin film is formed.

The first electrode 206 is connected to the transimpedance amplifier 207 and the phase monitor 210 of the nanopore forming device. The transimpedance amplifier 207 converts a current i carried through the first electrode 206 into a voltage signal $V_o$. To a reference terminal of the transimpedance amplifier 207, a modulated bias voltage $V_b$ is applied from the modulation voltage source 209. The transimpedance amplifier 207 operates such that the bias voltage $V_b$ applied to the reference terminal is equal to a voltage $V_e$ at a current input terminal. Thus, the voltage $V_e$ is also modulated suitable for bias voltage $V_b$. Supposing that a feedback resistance of the transimpedance amplifier 207 is $R_f$, the output voltage $V_o$ of the transimpedance amplifier is expressed by $V_o = i*R_f + V_b$. A differential amplifier 212 subtracts the component of the bias voltage from $V_o$, and hence extracts only information on the current component i carried through the thin film. The phase monitor 210 converts a difference between a phase of a modulation voltage $V_v$ applied to the first electrode 206 and a phase of $V_i = i*R_f$ into a voltage $V_{pd}$.

FIG. 5 is a diagram of the operating waveform the phase monitor 210. Here, it is assumed that a sine wave is applied as the modulation voltage $V_v$, and a nanopore is opened at time $T_{31}$. As described above, after the nanopore is opened, the advance of the phase of the current is dropped, and hence the phase of $V_i$ is delayed at time $T_{31}$. The input signals $V_v$ and $V_i$ are respectively converted into pulse waveforms $V_{vd}$ and $V_{id}$ by comparators. Supposing that the phase of $V_v$ and the phase of $V_i$ are the same, the waveforms of $V_{vd}$ and $V_{id}$ are completely matched, and when the phase is displaced at an angle of 180 degrees, the waveforms of $V_{vd}$ and $V_{id}$ are in inverted forms. $V_{vd}$ and $V_{id}$ are converted into the voltage signal $V_{pd}$ at an Exclusive NOR logic circuit and a lowpass filter in the subsequent stage. Here, when the phases of $V_{vd}$ and $V_{id}$ are matched, a duty cycle of the output of the Exclusive NOR circuit is at the maximum, and hence the output voltage $V_{pd}$ of the lowpass filter is increased. When the phases of $V_{vd}$ and $V_{id}$ are displaced, the duty cycle of the output of the Exclusive NOR circuit is decreased correspondingly, and hence $V_{pd}$ is decreased. Consequently, as $V_{pd}$, a voltage corresponding to the phase difference between $V_v$ and $V_i$ is outputted.

When the comparator 211 detects that $V_{pd}$ exceeds a threshold $V_{ref}$, the switch 208 is switched to a standby voltage $V_{stby}$ to stop the supply of the modulation voltage to the reference terminal of the transimpedance amplifier 207. As described above, $V_{stby}$ is a minute DC voltage or modulation voltage that does not change the size of a nanopore or the same voltage at the common electrode 205 (in the drawing, it is referred to as ground potential). Consequently, the application of stress to the thin film 201 is reduced, and an increase in a nanopore diameter is prevented.

According to such a configuration, the nanopore opening is monitored real time, and when the amount of change in the phase of the current exceeds the threshold, the application of the modulation voltage is automatically stopped. Since there is no current monitor period in which nanopore opening is monitored, a nanopore can be opened at high speed. As another effect, since the application of stress to a nanopore can be electrically stopped, the termination process after the nanopore is opened is performed at high speed, compared with the case in which a nanopore is formed by semiconductor processes, such as wet etching, and hence an unnecessary increase in the nanopore diameter can be prevented. A method with which the nanopore diameter is increased to finally form a desired size will be described later, separately.

Figure 6:
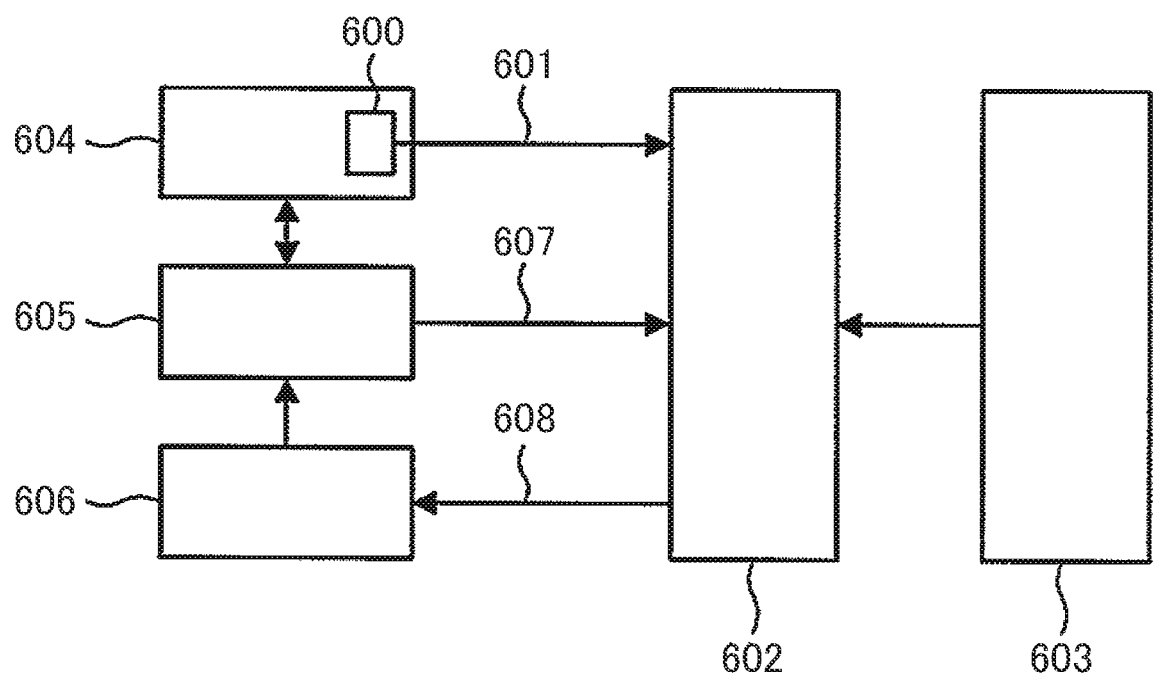
FIG. 6 is a schematic diagram of an exemplary modification of a first embodiment.

FIG. 6 is a schematic diagram of an exemplary modification of the nanopore forming device according to the first embodiment. FIG. 6 schematically shows the device configuration shown in FIG. 4, and additionally includes an information storage unit 600 and a database 603. In FIG. 6, 604 indicates a chip, including the thin film 201 and the chip 200 in FIG. 4. 605 indicates a phase monitor unit, including the transimpedance amplifier 207 and the phase monitor 210 in FIG. 4. 606 indicates a modulation voltage source, including the modulation voltage source 209, the switch 208, and the standby power supply $V_{stby}$ in FIG. 4. A control circuit 602 has a function corresponding to the comparator 211 and the reference voltage $V_{ref}$ in FIG. 4.

Figure 7:
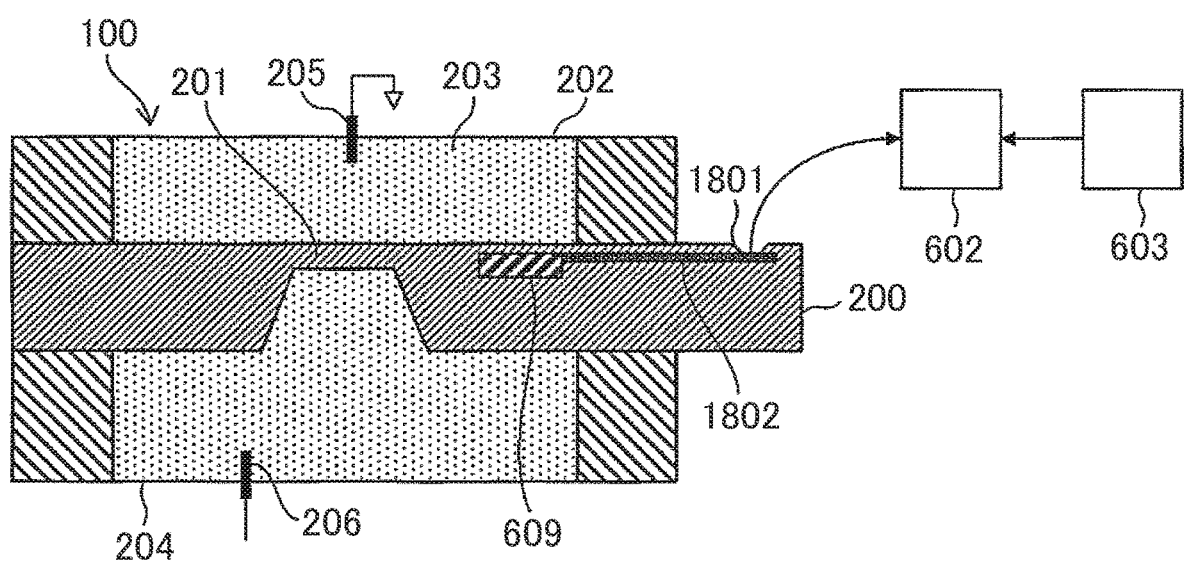
FIG. 7 is a diagram of an exemplary configuration of an information storage unit.

The information storage unit 600 is included in the chip 200 of the nanopore device 100. The control circuit 602 makes reference to the database 603 based on information 601 read from the information storage unit 600, and determines the optimum modulation voltage to be outputted from the modulation voltage source 606. Parameters of the modulation voltage include types of waveforms (e.g. sine waves, square waves, ramp waves, and pulse waves), frequency, duty cycle, amplitude, and voltage offset, for example. Information held on the information storage unit 600 may be information of structure, such as materials configuring the thin film 201 and the thickness, may be impedance information on the thin film 201, or may be an ID that can identify a type of the thin film 201. The information storage unit 600 desirably has one-to-one correspondence with the chip 200. For example, as shown in FIG. 7, the information storage unit 600 may be integrally formed on the chip 200 as a memory device 609. Information stored on the memory device 609 is externally led through a wire 1802 and a pad 1801, and read out to the control circuit 602. The nanopore device 100, i.e., the chip 200 is exchanged every time when nanopore forming is finished. Thus, the chip 200 is integrally formed with the information storage unit 600 as described above, and hence the application of the modulation voltage that is not optimum can be prevented. Consequently, this contributes to improving an accuracy of nanopore forming. Note that in FIG. 7, units involved in nanopore forming are not shown for simplicity.

The database 603 records information relating to methods with which what kind of modulation voltage is applied to the thin film for highly accurately detecting nanopore opening corresponding to these pieces of information. Alternatively, the information storage unit itself holds the parameters of the modulation voltage. In this case, there is a merit that the database 603 is unnecessary. Whatever the case may be, it is necessary to flexibly change the modulation voltage suitable for thin films for highly accurately forming nanopores. For example, when an excessive modulation voltage is applied regardless of a thin film having a small thickness, a sudden dielectric breakdown occurs, and this might form a pore in diameter larger than a desired diameter, or a plurality of nanopores might be formed on the thin film. Thus, the optimum modulation voltage has to be selected suitable for the structure of the thin film 201. The content to be stored on the database is the combination of the optimum values of parameters obtained beforehand by experiment using chips in various specifications. Alternatively, the content may be information based on general knowledge. For example, the dielectric breakdown voltage of semiconductor oxide films is empirically known, which is about 1 V/1 nm. Thus, the amplitudes necessary to form nanopores can be predicted to some extent corresponding to the thickness of a thin film.

On the other hand, it is also important to maximize the amount of change in the phase when the nanopore is formed for highly sensitive detection. For example, an amount $\Delta\theta$ of change in the phase before and after nanopore opening in a case in which a sine wave is applied can be expressed by Equation 3 below.

[Equation 3]

$$\Delta\theta = \left( \arctan\left( \frac{\omega C_M}{\frac{1}{R_P}} \right) - \arctan\left( \frac{\omega C_M}{\frac{1}{R'_P}} \right) \right) * 360/(2\pi) \quad (3)$$

Here, $R_P$ and $R_P'$ are the resistance values of the thin film before nanopore opening and after opening.

Figure 8:
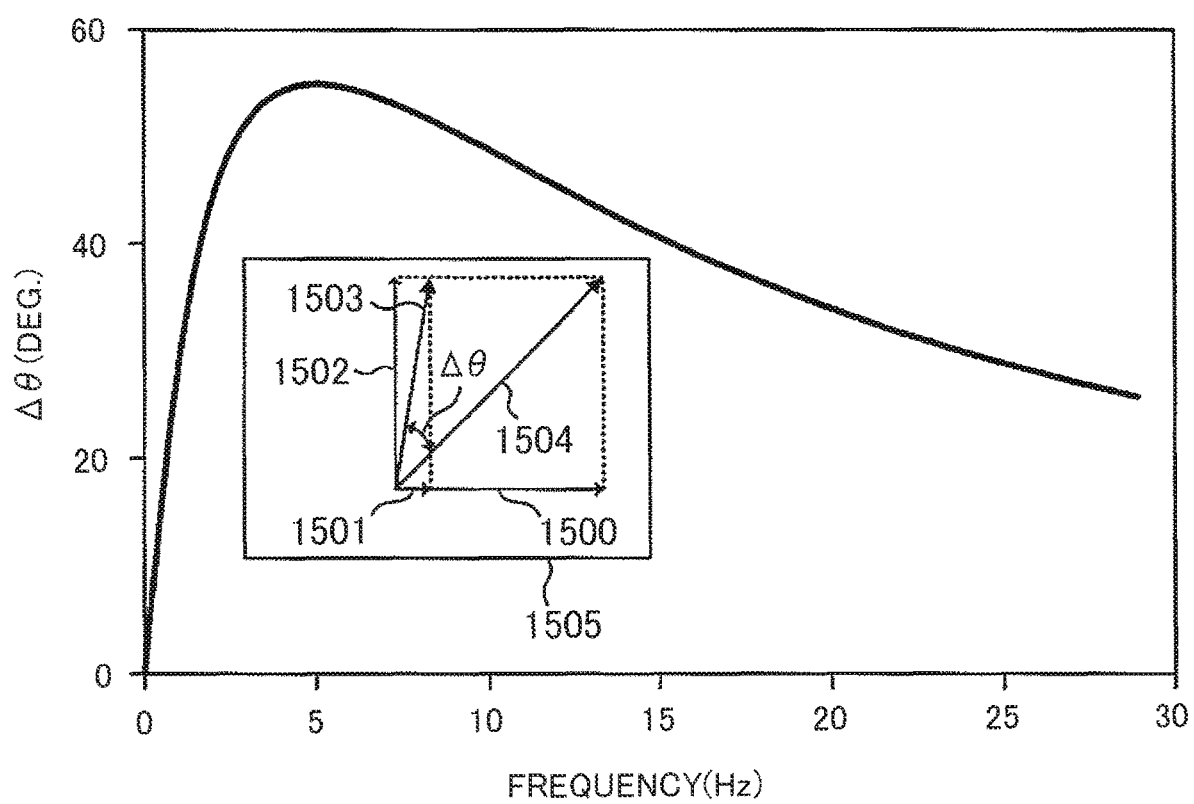
FIG. 8 is a diagram of a computing example of an optimum application frequency.

FIG. 8 is a diagram of a computing example of an optimum application frequency. FIG. 8 shows frequency dependence of the amount $\Delta\theta$ of change in the phase found from Equation 3, where $C_M$=10 pF, $R_P$=10 GΩ, and $R_P'$=1 GΩ. In FIG. 8, 1505 indicates a current component carried through the thin film in vector. The current carried through the capacitance component of the thin film is expressed by 1502, the current carried through the resistance component $R_P$ of the thin film before nanopore opening is expressed by 1501, and the current carried through the resistance component $R_P'$ of the thin film after nanopore opening is expressed by 1500. 1503 is the combined component of 1502 and 1501, and 1504 is the combined component of 1502 and 1500. The phase difference $\Delta\theta$ found by Equation 3 is the phase difference between the current vectors 1503 and 1504 before and after nanopore opening. As shown in FIG. 8, a frequency is present at which the phase difference $\Delta\theta$ is maximized. In this example, when a nanopore is formed at a modulation voltage around 5 Hz, the phase difference $\Delta\theta$ can be maximized. When the phase difference is increased before and after nanopore opening, this facilitates detection at the phase monitor circuit, and hence nanopore forming can be more highly accurately detected.

Since $C_M$, $R_P$, $R_P'$ in Equation 3 depend on the structure of the thin film that is used or a type or concentration of an electrolytic solution, optimum frequencies for a plurality of combinations of $C_M$, $R_P$, $R_P'$ are calculated in advance using Equation 3, and stored on the database 603. With such a configuration, the optimum pore forming is made possible corresponding to various types of thin films or liquid solution conditions. Note that as described above, the modulation voltage does not have to necessarily be a sine wave. The types of waveforms are non-limiting as long as phase information can be extracted, such as triangular waves, ramp waves, square wave, or the combinations of these waves.

Figure 9:
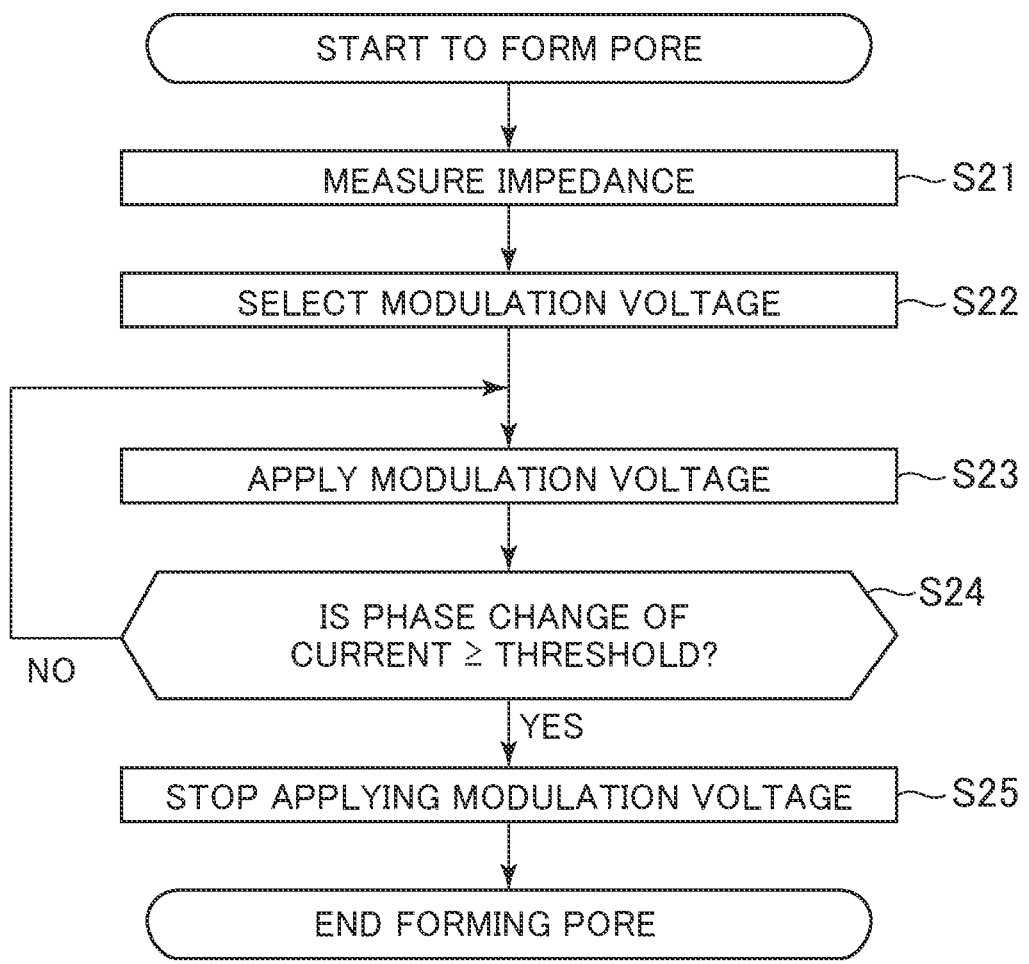
FIG. 9 is a flowchart of the exemplary modification of the first embodiment.

FIG. 9 is a flowchart of the exemplary modification of the first embodiment. In FIG. 9, there are characteristics in which instead of additionally providing the information storage unit 600 on the chip of the nanopore device, the impedance of the thin film is measured before nanopore opening (S21) and the optimum modulation voltage is selected corresponding to the measurement result (S22). As described in FIG. 6, in the selection of the optimum modulation voltage, a database that records information on the optimum modulation voltage corresponding to the impedance may be used, or the parameters of the modulation voltage is determined on the spot using Equation 3. After that, the selected modulation voltage is applied to the thin film (S23). The phase of the current is monitored during the application of the modulation voltage, after the amount of change in the phase exceeds the threshold information (S24), the application of the modulation voltage is stopped (S25), and nanopore opening is ended. According to such a configuration, the optimum pore forming is made possible corresponding to various types of thin films or the liquid solution conditions.

Second Embodiment

In this embodiment, the modulation voltage for nanopore forming will be described.

Figure 10:
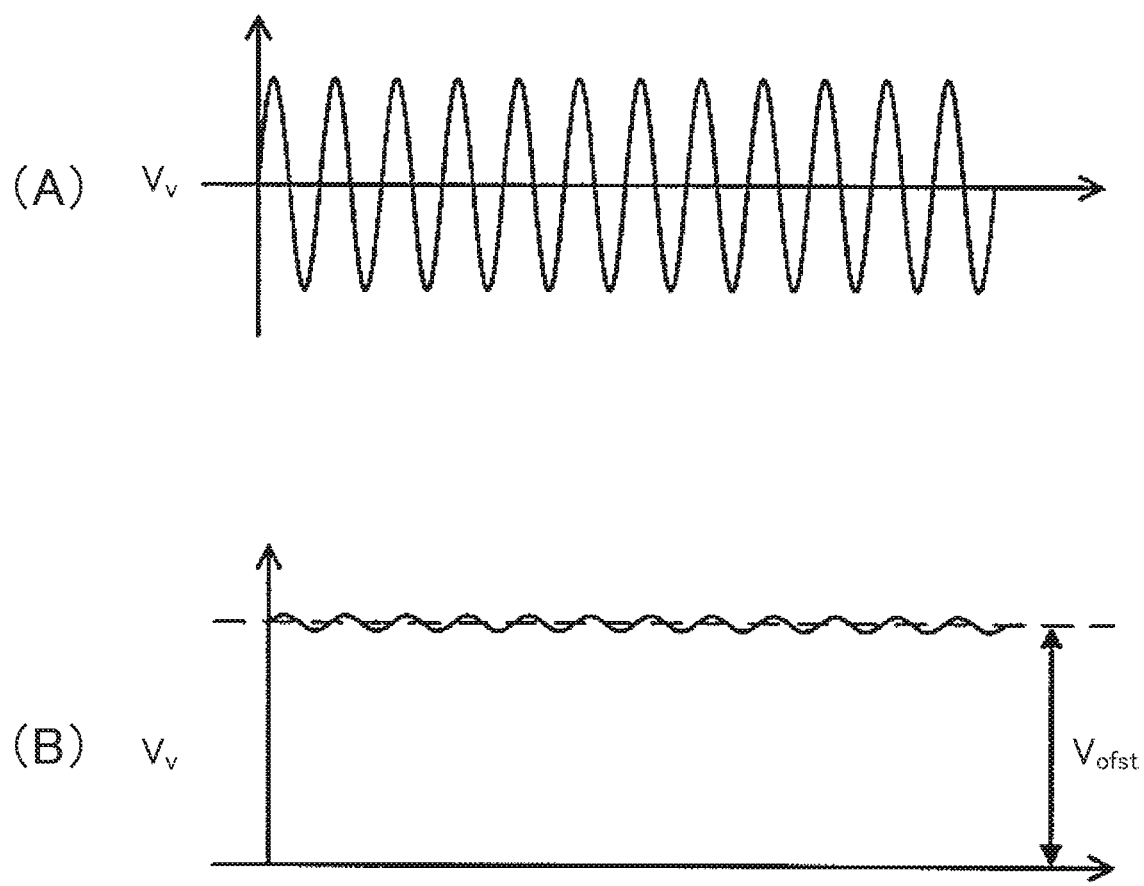
FIG. 10 is a waveform diagram of an exemplary modulation voltage for forming a nanopore.

FIG. 10(A) is a waveform diagram of an exemplary modulation voltage for nanopore forming. In this nanopore forming method, in the method described in the first embodiment, an AC voltage including the origin point in the center is applied as a modulation voltage. It is reported that the voltage-to-current characteristics after nanopore opening depends on a cross sectional shape of the formed nanopore. For example, Patent Literature 1 described above reports that when an alternating current is applied, the cross sectional shape is symmetry to a vertical direction, and hence the voltage-to-current characteristics become linear. Improving the linearity of the voltage-to-current characteristics of the nanopore can bring expectations that improve the accuracy of determining DNA sequences.

Figure 11:
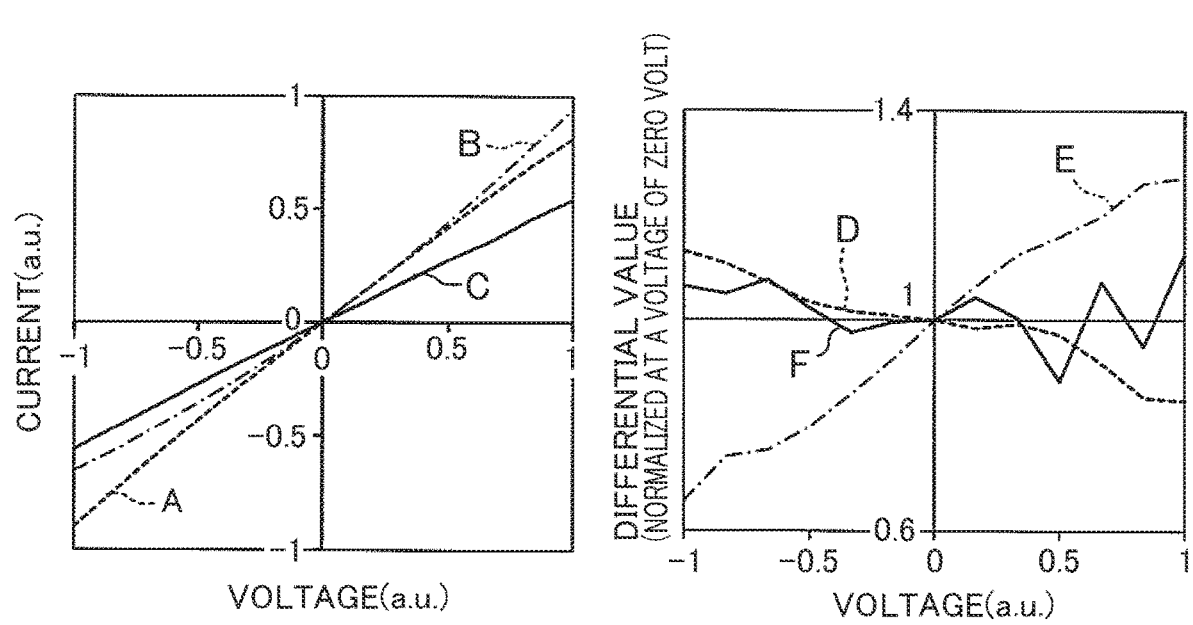
FIG. 11 is a diagram of a relationship between types of modulation voltage to be applied to form a nanopore and current-to-voltage characteristics obtained by the opened nanopore.

FIG. 11 is a diagram of the relationship between the types of modulation voltage to be applied to form a nanopore and the current-to-voltage characteristics obtained by the opened nanopore. In FIG. 11, A, B, and C are current-to-voltage characteristics obtained from a nanopore opened by applying a positive voltage pulse alone, a nanopore opened by applying a negative voltage pulse alone, and a nanopore opened by applying a sine wave alternating current including the origin point as the center. D, E, and F are the plots of the differential values of the waveforms. As shown from FIG. 11, a nanopore is opened using the sine wave alternating current including the origin point as the center, and hence the effect that improves the linearity of the current-to-voltage characteristics is achieved.

FIG. 10(B) is a waveform diagram of an exemplary modification of the modulation voltage for nanopore forming. In this nanopore forming method, a DC offset voltage $V_{ofst}$ is added to the modulation voltage described in FIG. 10(A). There are characteristics in which a nanopore is opened by applying stress mainly using the DC offset voltage $V_{ofst}$, a modulation voltage is added for detecting opening, and the phase is monitored. Note that as shown in FIG. 4, a capacitive element is additionally provided at the input of the phase monitor circuit 210 to provide AC coupling, and hence the current component due to the DC offset voltage $V_{ofst}$ can be removed. Even though the offset voltage $V_{ofst}$ is added, a phase change in the current can be correctly monitored. According to such a configuration, the state is achieved in which stress is always applied to the thin film, and hence nanopore opening is further accelerated.

Third Embodiment

A nanopore forming method according to the embodiment has a phase (Phase 2) in which a nanopore is enlarged to a desired size in addition to a phase (Phase 1) in which a nanopore is formed by the method described in the first embodiment.

Figure 12:
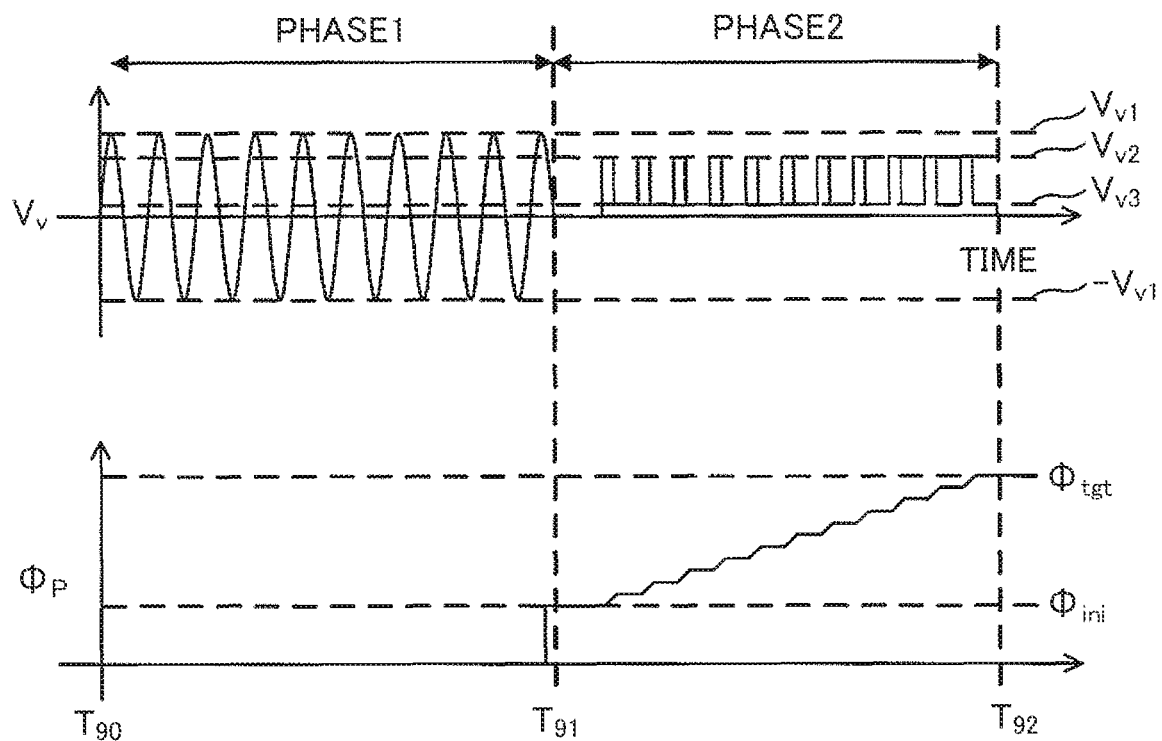
FIG. 12 is a waveform diagram of examples of time variation in an application voltage and a diameter of the nanopore.

FIG. 12 is a waveform diagram of the application voltage $V_v$ and an exemplary time variation of a diameter $\varphi_P$ of a nanopore by the nanopore forming method according to the third embodiment. In FIG. 12, the target pore diameter that is finally formed is expressed by $\varphi_{tgt}$. First, in Phase 1 that is started at time $T_{90}$, a nanopore is formed by applying a sine wave ac voltage. Here, the pore diameter immediately after opened at time $T_{91}$ is expressed by $\varphi_{ini}$. In order to accurately achieve the final pore diameter $\varphi_{tgt}$, desirably, the application waveform in Phase 1 is adjusted such that the pore diameter $\varphi_{ini}$ immediately after opened is smaller than the target pore diameter $\varphi_{tgt}$, a weak stress is applied in Phase 2 after that, and the diameter is increased to the target pore diameter $\varphi_{tgt}$. Desirably, the stress applied to the thin film in Phase 2 that is an increasing phase is weaker than the stress applied to the thin film in Phase 1 that is the opening phase. This is important to prevent new pores, which are the second and third ones, from being formed. The pore diameter is gently increased, and hence the final pore diameter can be accurately matched to $\varphi_{tgt}$.

The waveform to be applied in Phase 2 may be a sine wave subsequently. However, in order to weaken the stress applied to the thin film, desirably, the peak voltage is lower than in Phase 1. Instead of the sine wave, a pulse voltage may be applied. Desirably, the pulse to be applied has a peak voltage lower than the sine wave in Phase 1 or has a shorter pulse duration, and hence effective energy supplied to the thin film and the nanopore is reduced to weaken stress for gently increasing the pore diameter. In FIG. 12, after the sine wave at a pulse height $V_{V1}$ is applied in Phase 1, in Phase 2, a rectangular pulse at $V_{V2}$ lower than $V_{V1}$ is applied to increase the pore, a voltage $V_{V3}$ lower than $V_{V2}$ is applied, the current is monitored, and hence the pore diameter is confirmed. At a point in time (time $T_{92}$) at which after the confirmation that the value of the current reaches the target value and a desired pore diameter is achieved, the application of stress is stopped.

According to such a configuration, a pore can be opened at high speed by applying a sine wave and phase monitoring, and the pore can be accurately increased in a desired pore diameter. In the configuration in FIG. 12, the overhead of the current monitor period occurs during the period of Phase 2. However, in Phase 1, monitoring the phase of the ac voltage eliminates the monitor period of the current, and hence a nanopore can be opened at high speed. Thus, total time is shortened, and a nanopore in a desired pore diameter can be formed at high speed, compared with a conventional method in which the current is monitored at every application of pulses from the opening stage.

Fourth Embodiment

Figure 13:
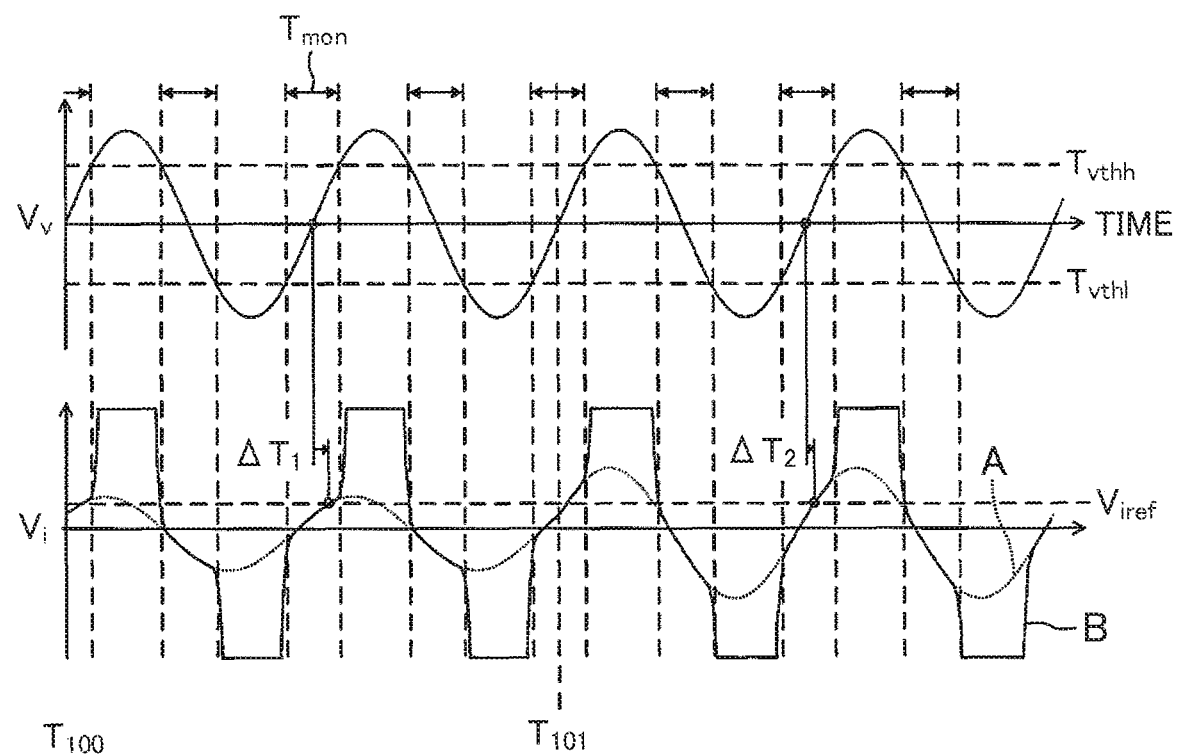
FIG. 13 is a waveform diagram illustrating examples of a timing of extracting phase information on the current in forming nanopores.

FIG. 13 is a waveform diagram illustrating examples of the timing of extracting the phase information on the current in forming nanopores. As described above, when the thickness of the thin film is reduced, a leakage current due to the tunnel phenomenon is carried noticeably. It is described that the leakage current is the phenomenon that is observed on insulating films having a film thickness of a few nanometers, such as the gate oxide film of a MOS transistor. When the film thickness is reduced, the leakage current is exponentially increased (e.g. see Lee et al., Gate oxide leakage current analysis and reduction for VLSI circuits, IEEE Trans. on VLSI Systems, 2004). The similar phenomenon also occurs on a thin film on which a nanopore is formed. Thus, when a nanopore is formed on a thin film that is specifically thin, a correct current value might not be monitored due to a leakage current.

FIG. 13 is a diagram of the simulation result that a nanopore is formed at time $T_{101}$, plotting a change in the output voltage $V_i$ of the differential amplifier 212 to the modulation voltage $V_v$ for opening a nanopore in FIG. 4. In the case in which a leakage current can be ignored, the current waveform is as A. However, in the case in which the thickness of the thin film is thin, a leakage current is increased in a time period in which the absolute value of the modulation voltage $V_v$ is large. Thus, $V_i$ is periodically suddenly increased as shown in B, and the waveform is like a waveform that is saturated around the power supply voltage of the differential amplifier. Such a leakage current makes correct evaluation of the phase difficult, and forming a pore might not be detected.

Therefore, in the embodiment, the phase information is extracted using the waveform $V_i$ alone in a period expressed by $T_{mon}$ in which the leakage current is less affected. Specifically, a threshold $V_{iref}$ is preset, and a time difference $\Delta T$ between time at which $V_i$ crosses $V_{iref}$ and timing at which the absolute value of the modulation voltage $V_v$ is in a voltage rang including no peak voltage, e.g. time at which the modulation voltage $V_v$ crosses zero is detected as a phase difference. Before a nanopore is formed (time $T_{100}$ to $T_{101}$), the difference is $\Delta T_1$, whereas after the nanopore is opened (after time $T_{101}$), the amount of the advance of the phase is reduced, which is $\Delta T_2$. This change in the phase is detected to stop the application of the modulation voltage. Thus, even in thin films having a thin film thickness and having a noticeable influence of the leakage current, nanopore opening can be correctly detected.

Fifth Embodiment

Figure 14:
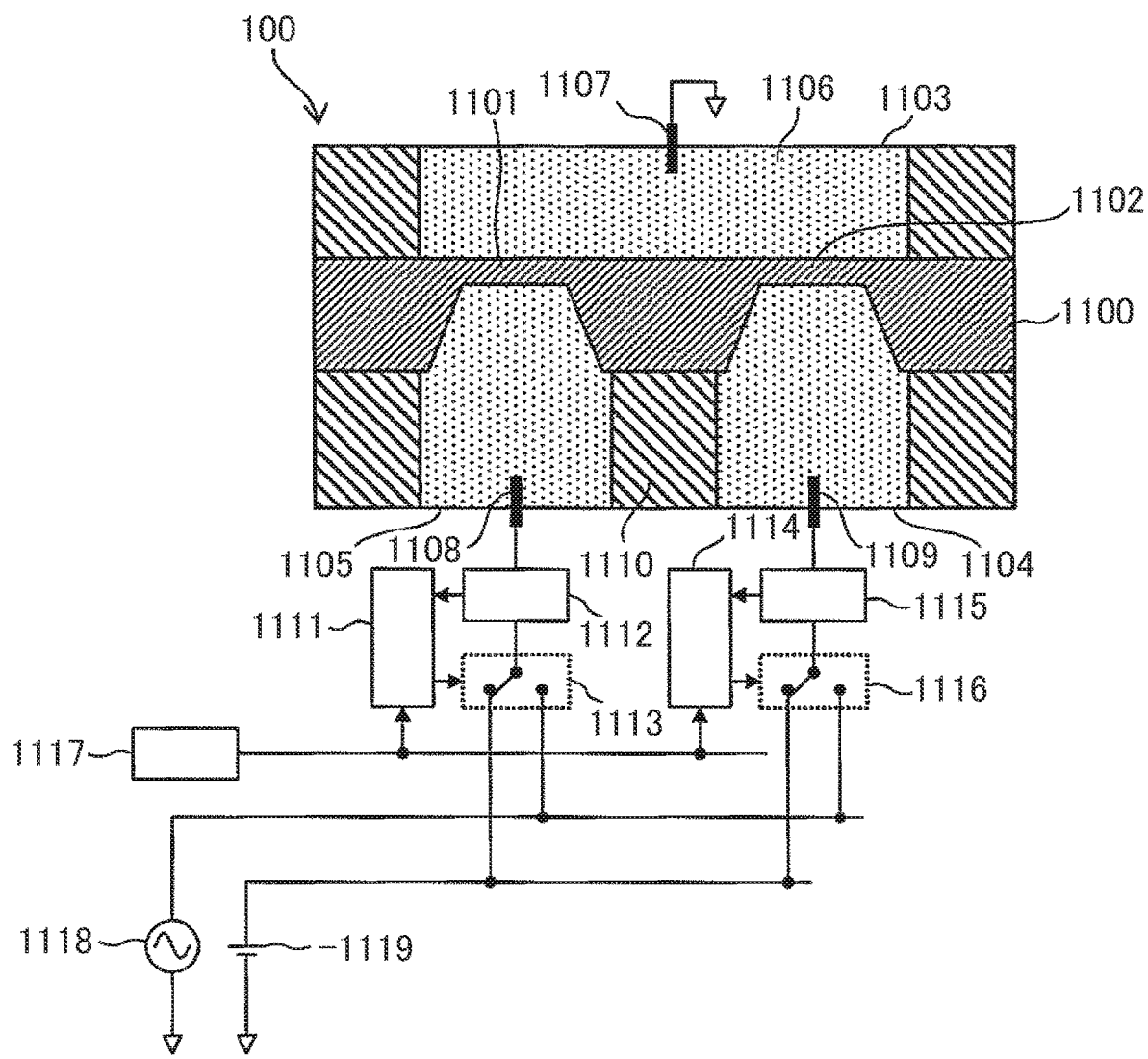
FIG. 14 is a diagram of an exemplary configuration of a nanopore forming device.

FIG. 14 is a diagram of an exemplary configuration of a nanopore forming device according to a fifth embodiment.

A nanopore device 100 includes a chip 1100, a common chamber 1103, and a first chamber 1105 and a second chamber 1104 that are individual chambers. The chambers are filled with an electrolytic solution 1106. The chip 1100 isolates the electrolytic solution in the common chamber 1103 from the electrolytic solution in the first chamber 1105, and isolates the electrolytic solution in the common chamber 1103 from the electrolytic solution in the second chamber 1104. The first chamber is isolated from the second chamber by a wall 1110. The common chamber 1103 has a common electrode 1107. The first chamber 1105 has a first electrode 1108. The second chamber 1104 has a second electrode 1109. The electrodes are immersed in the electrolytic solution 1106. On the chip 1100, a first thin film 1101 and a second thin film 1102 are formed. The first thin film 1101 is in contact with the electrolytic solution in the common chamber 1103 and the first chamber 1105. The second thin film 1102 is in contact with the electrolytic solution in the common chamber 1103 and the second chamber 1104. The thin film is considerably thin, having a thickness ranging from sub-nanometers to a few tens nanometers, for example, suitable for a biomolecular sample that is a measurement target.

The nanopore forming device according to the embodiment includes a set of a phase monitor, a switch, and a control circuit exclusive for the individual thin films prepared for the number of thin films formed on the chip 1100 and a phase threshold 1117, a modulation voltage source 1118, and a standby power supply 1119 common in all the thin films. In the case is shown in which two thin films are provided for explanation. However, naturally, the embodiment is also applicable to the case in which the number of thin films formed on a chip is three or more.

To the first electrode 1108 of the nanopore device 100, a switch 1113 is connected through a phase monitor 1112 of the nanopore forming device. The control circuit 1111 compares the phase information from the phase monitor 1112 with the phase threshold 1117 to detect nanopore opening, switches the switch 1113 from the modulation voltage source 1118 side to the standby power supply 1119 side, and hence stops the application of the modulation voltage for forming a nanopore. Similarly, to the second electrode 1109 of the nanopore device 100, a switch 1116 is connected through a phase monitor 1115 of the nanopore forming device. The control circuit 1114 compares phase information from the phase monitor 1115 with the phase threshold 1117 to detect nanopore opening, switches the switch 1116 from the modulation voltage source 1118 side to the standby power supply 1119 side, and stops the application of the modulation voltage for forming a nanopore. A modulation voltage is applied from the first electrode 1108 to the first thin film 1101, and a modulation voltage is applied from the second electrode 1109 to the second thin film 1102 independently.

According to such a configuration, pores are independently opened on the first thin film 1101 and the second thin film 1102 at the same time, and hence integrated pores can be opened at high speed. The control circuits are included independently for each of the thin films, and hence the application of the modulation voltage can be stopped any time on the place where a pore is opened. Thus, an increase in the nanopore diameter can be prevented. On the other hand, the phase threshold 1117, the modulation voltage source 1118, and the standby power supply 1119 are provided in common. Thus, the amount of necessary circuits is reduced to achieve a reduction in space and costs.

Sixth Embodiment

Figure 15:
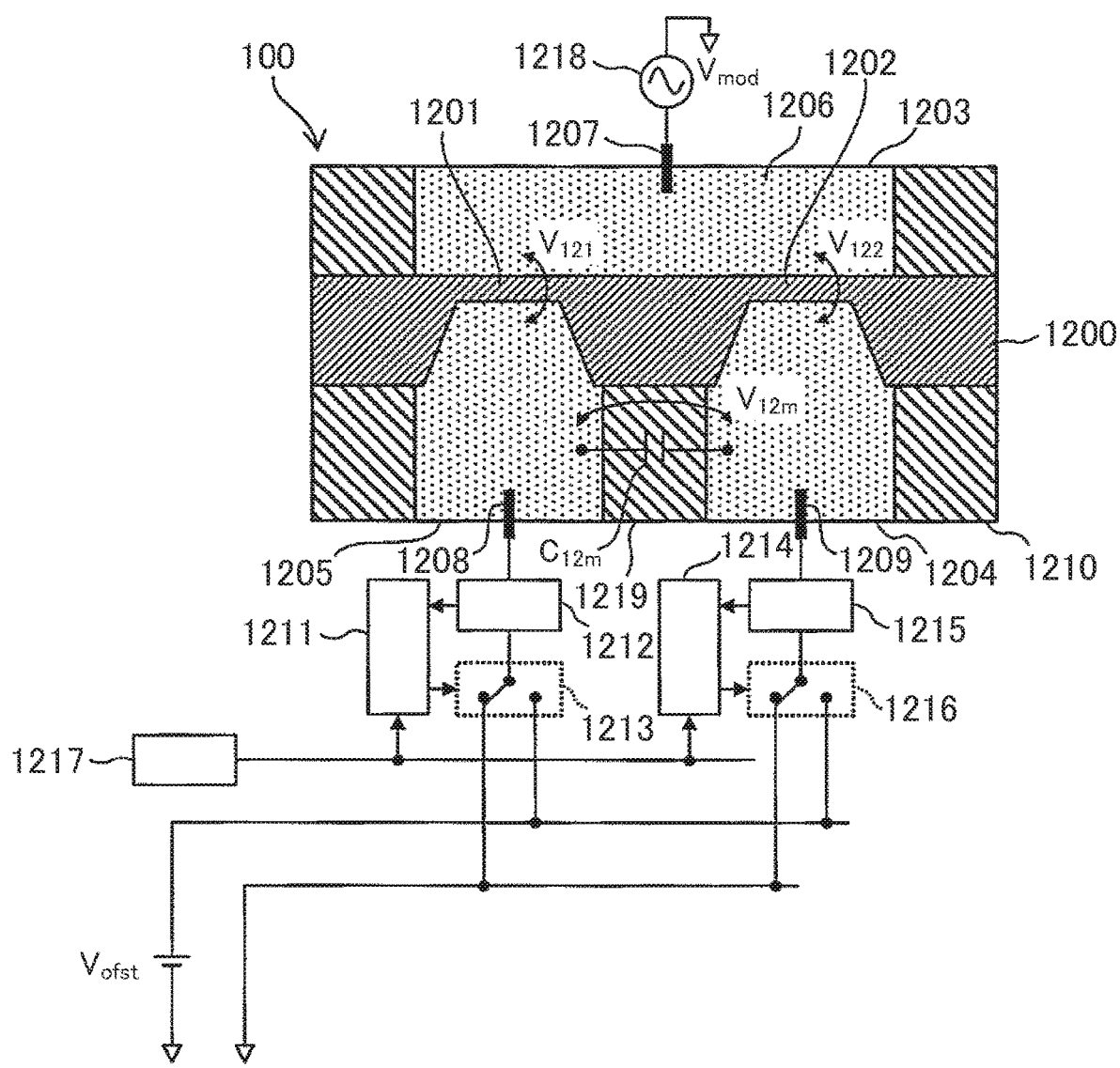
FIG. 15 is a diagram of an exemplary configuration of a nanopore forming device.

FIG. 15 is a diagram of an exemplary configuration of a nanopore forming device according to according to a sixth embodiment.

In the nanopore forming device according to the embodiment, in the nanopore forming device described in the fifth embodiment, a modulation voltage is applied to a common electrode 1207 instead that a modulation voltage is applied to a first electrode 1208 and a second electrode 1209 of a nanopore device. On the other hand, a offset voltage $V_{ofst}$ is applied to the first electrode 1208 and the second electrode 1209 of the nanopore device. At this time, a voltage $V_{121}$ applied to a thin film 1201 and a voltage $V_{122}$ applied to a thin film 1202 are each the sum of a modulation voltage $V_{mod}$ and thane offset voltage $V_{ofst}$.

Here, as in FIG. 10(B), stress application for pore forming is performed mainly using the DC offset voltage $V_{ofst}$, and the modulation voltage $V_{mod}$ is used for detecting opening. For example, in the case in which nanopore opening on the thin film 1201 is detected, the switch is switched to turn the offset voltage $V_{ofst}$ to 0 V, similarly to the fifth embodiment. In this case, the voltage applied to the thin film 1201 is $V_{mod}$ alone, the application of stress to the thin film is greatly reduced, and hence an unintentional increase in the nanopore diameter can be avoided.

Another effect of the sixth embodiment is to prevent integration from being disturbed. Referring to FIGS. 14 and 15, this effect will be described. When the integration of the nanopore device is advanced, the thickness of the wall 1219 between the first chamber 1205 and the second chamber 1204 is reduced, and parasitic capacitance $C_{12m}$ is increased. In the sixth embodiment, the DC voltage ($V_{ofst}$ or 0 V) alone is always applied to the first electrode 1208 and the second electrode 1209 of the nanopore device, and hence disturbing through the parasitic capacitance $C_{12m}$ does not occur.

On the other hand, in the case in which the first electrode side and the second electrode side are modulated as in FIG. 14, crosstalk occurs between the adjacent chambers through the parasitic capacitance. In FIG. 14, the situations are considered in which opening of the nanopore is finished on the second thin film 1102, the application of the modulation voltage is stopped, but no nanopore is opened yet on the first thin film 1101. At this time, the modulation voltage is still continuously applied to the first electrode 1108 on the first thin film 1101 side. The stress is still continuously applied to the second thin film 1202 through the parasitic capacitance $C_{12m}$. Consequently, the diameter of the nanopore formed on the second thin film 1102 might be increased (disturbed). The nanopore forming method according to according to the sixth embodiment is made in consideration of such a problem. Even though the integration of the nanopore device is advanced, disturbing between the adjacent chambers in the opening is eliminated, and hence nanopore forming can be implemented more highly accurately.

Seventh Embodiment

Figure 16:
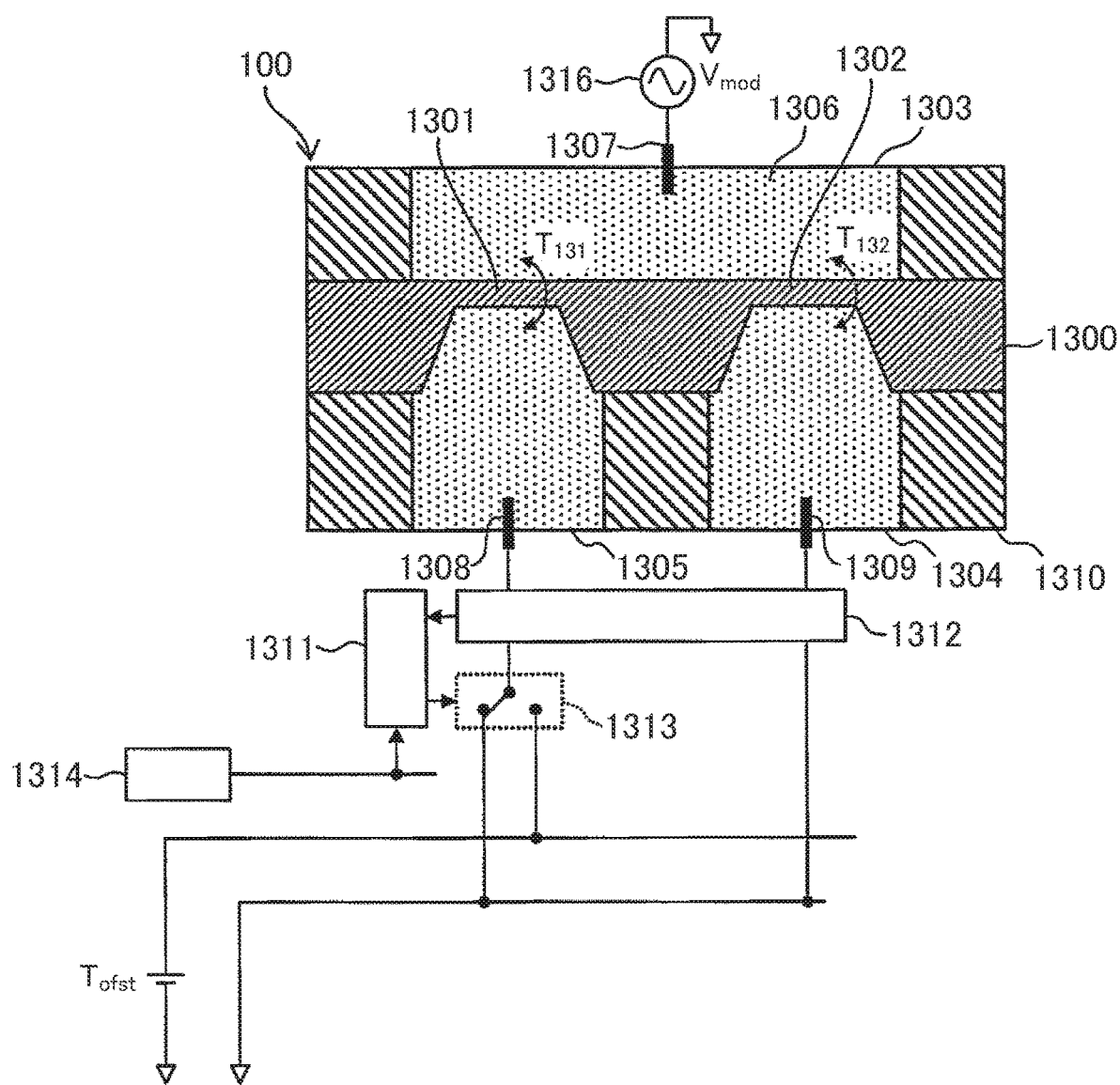
FIG. 16 is a diagram of an exemplary configuration of a nanopore forming device.

FIG. 16 is a diagram of an exemplary configuration of a nanopore forming device according to a seventh embodiment.

The nanopore forming device according to the embodiment detects nanopore opening by the difference from the phase of a current carried through a reference thin film. Specifically, in FIG. 16, in forming a nanopore on a first thin film 1301 of a nanopore device 100, a phase comparator 1312 detects the difference between the phase of a current carried through the first thin film 1301 and the phase of a current carried through a second thin film 1302. At a point in time when the difference exceeds a preset threshold 1314, a control circuit 1311 of the nanopore forming device switches a switch 1313. Here, a voltage $V_{131}$ applied to the first thin film 1301 before the nanopore forming is the sum of a of modulation voltage $V_{mod}$ and a DC offset voltage $V_{ofst}$ of the common electrode 1307. On the other hand, since a low DC offset voltage lower than $V_{ofst}$, i.e., in this example, a voltage of 0 V is always applied to a second electrode 1309, a voltage $V_{132}$ applied to the second thin film 1302 is the modulation voltage $V_{mod}$ of the common electrode 1307 alone. Since a nanopore is opened after the application of the DC offset voltage $V_{ofst}$, no nanopore is formed on the second thin film 1302. With the use of the AC coupling phase monitor circuit 210 shown in FIG. 4, from the current components of the current carried through the first thin film 1301 and the current carried through the second thin film 1302, the current components due to the modulation voltage $V_{mod}$ are alone extracted, and then the phases can be compared.

Figure 17:
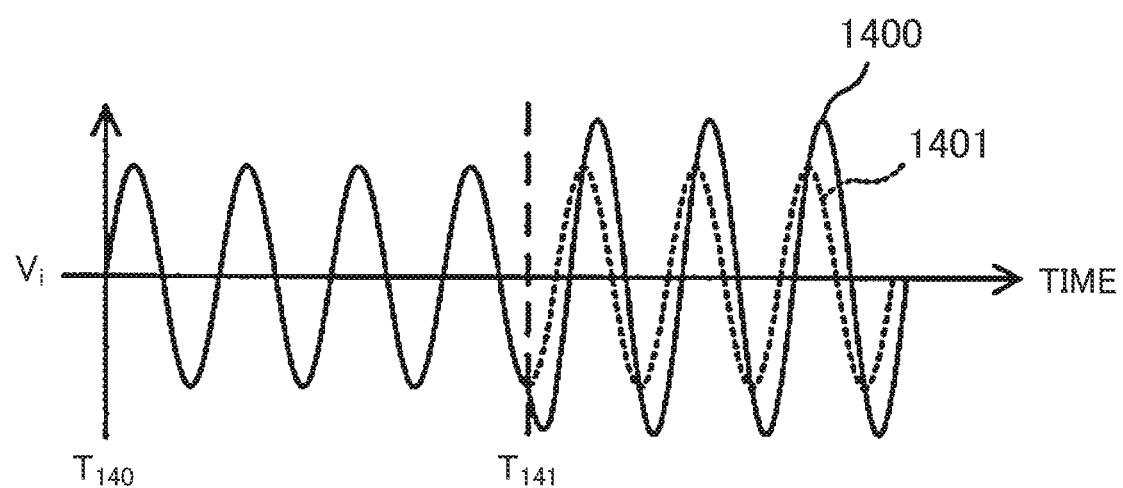
FIG. 17 is a diagram of exemplary operating waveforms of the nanopore forming device.

FIG. 17 is a diagram of exemplary operating waveforms of the nanopore forming device according to the embodiment. FIG. 17 shows time waveforms when the current carried through the first thin film 1301 of the nanopore device 100 and the current carried through the second thin film 1302 are converted into the voltage $V_i$. Here, it is assumed that at time $T_{141}$, a nanopore is formed on the first thin film 1301. A waveform 1400 is the waveform of the current carried through the first thin film 1301, and the amplitude and the phase are changed by forming a nanopore at time $T_{141}$. The waveform 1401 is the waveform of the current carried through the second thin film 1302. As described above, since the modulation voltage $V_{mod}$ alone is applied to the second thin film, no dielectric breakdown occurs and no phase neither nor amplitude is changed as long as the amplitude of the modulation voltage $V_{mod}$ is sufficiently small. Basically, since the thin films 1301 and 1302 that formed on the same chip by semiconductor processes have the same material and the same thickness, the impedance before opening is almost equal. Thus, the nanopore forming can be detected more highly sensitively by detecting the phase difference between the waveforms 1400 and 1401.

Eighth Embodiment

Figure 18:
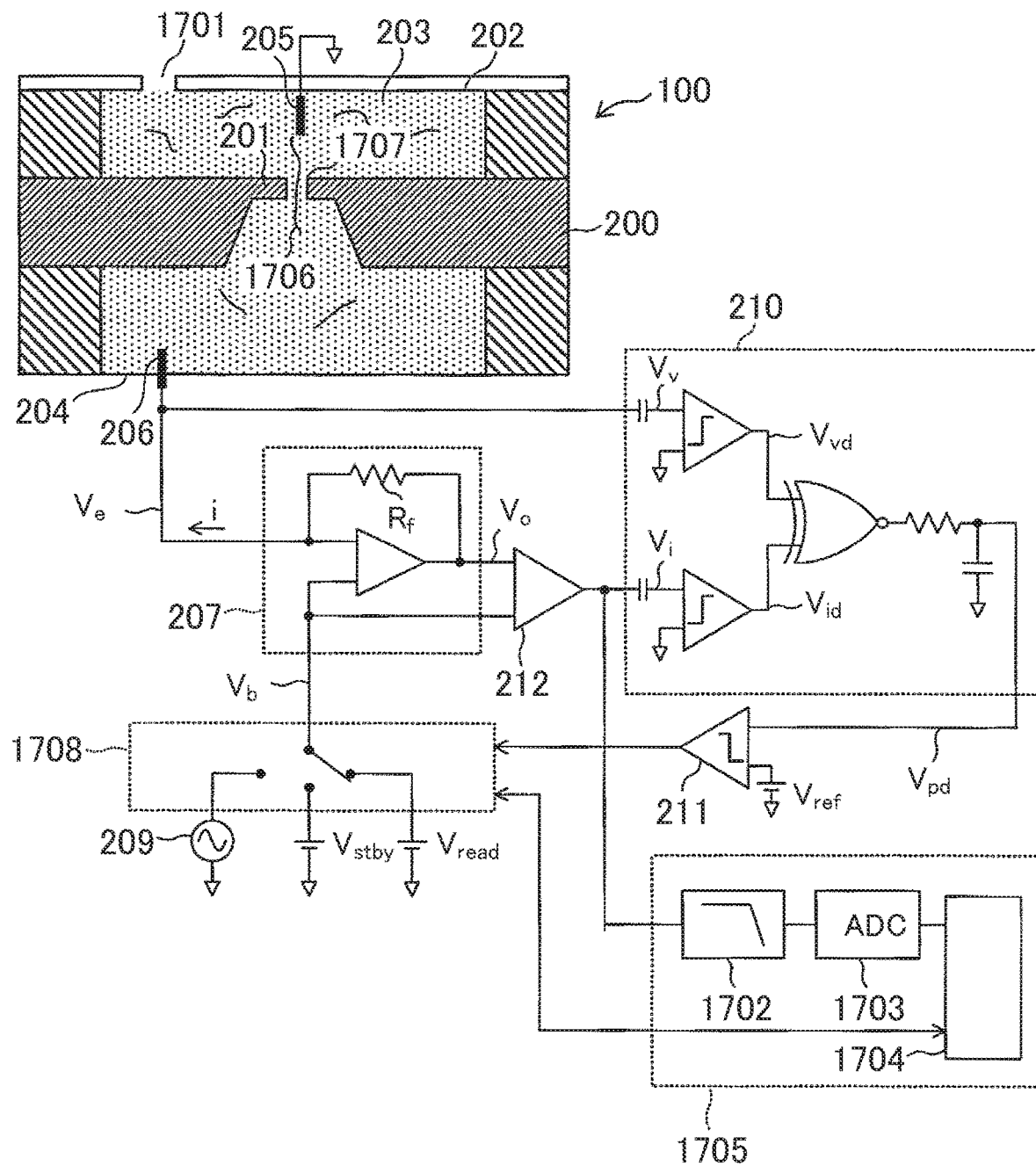
FIG. 18 is a diagram of an exemplary configuration of a nanopore forming device.

FIG. 18 is a diagram of an exemplary configuration of a biomolecule measuring apparatus according to an eighth embodiment.

The biomolecule measuring apparatus according to the embodiment further includes a function that reads a DNA sequence in addition to the nanopore device and the nanopore forming device described in the first embodiment. Specifically, at the common chamber 202 of the nanopore device 100, an injection port 1701 that injects a liquid solution and a DNA sample that is a measurement target is included, and a measurement unit 1705 that identifies a DNA sequence. The measurement unit 1705 includes a filter circuit 1702 that cuts the radio frequency component of the output of the differential amplifier 212, an analog digital converter 1703, and a data processor 1704. The switch 1708 has a modulation voltage source 209 used in nanopore forming and standby power supply that applies a standby voltage $V_{stby}$, as well as a function that switches from a read power supply that applies a read voltage $V_{read}$ in measurement.

FIG. 18 is a diagram after a nanopore 1707 is formed on the chip 200 of the nanopore device 100 by the procedures described in the first embodiment. The data processor 1704 also has the function of monitoring the state of the switch 1708 and a control function. Upon switching the switch 1708 to $V_{stby}$, the data processor 1704 detects the completion of nanopore opening. After the nanopore 1707 is formed on the chip 200, the DNA sample that is a measurement target is injected from the injection port 1701 to the common chamber 202 of the nanopore device 100. After injecting the sample, the data processor 1704 switches the switch 1708 to the read voltage $V_{read}$. At this time, the voltage $V_e$ of the first electrode 206 is made equal to the read voltage $V_{read}$ by the function of the transimpedance amplifier 207. When the read voltage $V_{read}$ is made higher than the voltage of the common electrode 205, an electric field going from the first chamber 204 to the common chamber side 202 occurs near the nanopore 1707, and an ion current is carried in the nanopore 1707. Since DNA is negatively charged, DNA in the common chamber in 202 migrates to the first chamber 204 side through the nanopore 1707 due to this electric field. DNA 1706 expresses that the DNA 1706 is passing in the nanopore 1707.

When DNA is present in the nanopore 1707, a current (the blockade current) carried thorough the nanopore 1707 changes corresponding to the type of base present near the nanopore. Thus, a change in the current during which DNA is passing in the nanopore 1707 is measured, and hence the base sequence of DNA can be identified. The current i carried through the nanopore 1707 is converted into a voltage (i*$R_f$) by the transimpedance amplifier 207 and the differential amplifier 212. Thus, the output of the differential amplifier 212 is measured, and hence the DNA sequence can be identified. The filter circuit 1702 has a function that reduces noise components by narrowing the band of the output signal of the differential amplifier and a function that reduces alias that occurs at the ADC 1703 in the subsequent stage. After that signal is converted into a digital signal at the ADC 1703, the signal is finally converted into a base sequence at the data processor 1704.

According to such a configuration, nanopore forming and subsequent measurement of a blockade current can be sequentially performed in the same device. First, the measurement of the DNA sample can be started in a short time after nanopore forming, and hence the DNA blockade current can be measured at the optimum pore diameter. Supposing that in the case in which a pore is formed using another device and DNA is sequenced, the pore diameter of the nanopore might be changed. This is because stress is applied to the nanopore due to static electricity that occurs in transportation. Of course, although the nanopore can be formed in the stage of fabrication of the chip 200, the surface is oxidized due to the interaction with atmosphere or a reservation liquid solution in long-time reservation, and the nanopore diameter might be changed. Another advantage is that the transimpedance amplifier 207, the differential amplifier 212, the switch 1708, and the power supply circuit calculated be shared by nanopore forming units and the blockade current measurement unit, and hence the device size and fabrication costs can be reduced.

In FIG. 18, an example is shown in which the sample is injected on the common chamber 202 side. However, of course, such a configuration may be provided in which a sample injection port is provided on the first chamber 204 and the sample is injected to the first chamber 204 side. In this case, to the common electrode 205, the voltage applied to the first electrode 206 is dropped, and hence DNA can be introduced into the nanopore 1707.

Here, the case is described in which the individual chamber i.e., one first chamber 204 is provided. However, of course, the embodiment is also applicable to the nanopore device in which a plurality of individual chambers is provided separated by a wall. The embodiment is also applicable to the nanopore forming devices described in FIGS. 14, 15, and 16.

Exemplary Modifications of the Present Invention

Note that the present invention is not limited to the embodiments, and includes various exemplary modifications. For example, the foregoing embodiments are described in detail for easily understanding the present invention. The present invention is not limited to those including all the described configurations. A part of the configuration of an embodiment can be replaced by the configuration of another embodiment, and the configuration of another embodiment can be added to the configuration of an embodiment. Another configuration can be added to, removed from, or replaced by a part of the configurations of the embodiments.

REFERENCE SIGNS LIST

100: nanopore device
200: chip
201: thin film
202: common chamber
204: first chamber
205: common electrode
206: first electrode
207: transimpedance amplifier
208: switch
209: modulation voltage source
210: phase monitor
211: comparator
212: differential amplifier
600: information storage unit
602: control circuit
603: database
604: chip
605: phase monitor
606: modulation voltage source
1704: data processor
1705: measurement unit
1706: DNA
1707: nanopore

The invention claimed is:

1. A nanopore forming method that is a method of applying a voltage to a thin film to form a nanopore, comprising:
    applying a first modulation voltage to a thin film;
    comparing an amount of a change in a phase of a current carried through the thin film with respect to a phase of the first modulation voltage with a threshold; and
    upon detecting that the amount of the change in the phase exceeds the threshold, stopping application of the first modulation voltage.

2. The nanopore forming method according to claim 1, wherein a parameter of the first modulation voltage is determined corresponding to an impedance of the thin film.

3. The nanopore forming method according to claim 2, wherein before application of the first modulation voltage, the impedance of the thin film is measured.

4. The nanopore forming method according to claim 1, wherein the first modulation voltage is an alternating current as an origin point is a center.

5. The nanopore forming method according to claim 1, wherein the first modulation voltage has a DC offset.

6. The nanopore forming method according to claim 1, wherein after application of the first modulation voltage is stopped, a second modulation voltage applying stress weaker than the first modulation voltage is applied to the thin film to adjust a nanopore diameter.

7. The nanopore forming method according to claim 1, wherein the amount of the change in the phase is detected at timing in a voltage range in which the first modulation voltage includes no peak voltage.

8. The nanopore forming method according to claim 1, wherein: a plurality of the thin films is provided such that the thin films are isolated from each other by a wall, and the first modulation voltage is applied to each of the plurality of thin films;
    an amount of a change in a phase of a current carried through each of the thin films with respect to the phase of the first modulation voltage is individually compared with the threshold; and
    application of the first modulation voltage is stopped on a thin film on which the amount of the change in the phase exceeds the threshold is detected.

9. The nanopore forming method according to claim 8, wherein: the first modulation voltage has a DC offset;
    on the thin film on which the amount of the change in the phase exceeds the threshold is detected, after application of the first modulation voltage is stopped, a modulation voltage that the DC offset is removed from the first modulation voltage is kept applied.

10. The nanopore forming method according to claim 8, wherein the amount of the change in the phase of the current carried through each of the thin films is calculated based on a phase of a current carried through a reference thin film to which a second modulation voltage having an DC offset lower than an DC offset of the first modulation voltage is applied.

11. A nanopore forming device comprising:
a power supply configured to apply a modulation voltage between a first electrode and a second electrode disposed such that the first electrode and the second electrode sandwich a chip including a thin film on which a nanopore is formed;
a phase monitor configured to measure an amount of a change in a phase of a current carried between the first electrode and the second electrode with respect to a phase of the modulation voltage; and
a control circuit configured to stop application of the modulation voltage when the amount of the change in the phase of the current exceeds a threshold.

12. The nanopore forming device according to claim 11, wherein: a plurality of the second electrodes is disposed such that the second electrodes are isolated by a wall on one side of the chip; and
a plurality of the phase monitors and a plurality of the control circuits are individually provided for the plurality of the second electrodes.

13. The nanopore forming device according to claim 12, wherein the power supply includes
a first power supply configured to apply a modulation voltage to the first electrode, and
a second power supply configured to apply a DC voltage to the plurality of second electrodes.

14. A biomolecule measuring apparatus comprising:
a nanopore device having
a first chamber and a second chamber partitioned by a chip including a thin film, the first chamber and the second chamber being filled with an electrolytic solution,
a first electrode disposed in the first chamber, and
a second electrode disposed in the second chamber;
a modulation voltage source configured to apply a modulation voltage for nanopore opening between the first electrode and the second electrode;
a phase monitor configured to measure an amount of a change in a phase of a current carried between the first electrode and the second electrode with respect to a phase of the modulation voltage;
a control circuit configured to stop application of the modulation voltage when the amount of the change in the phase of the current exceeds a threshold;
a read voltage source configured to apply a read voltage for measuring a blockade current between the first electrode and the second electrode after a nanopore is formed on the thin film by application of the modulation voltage; and
an information processor configured to identify a sequence of a biomolecule injected into the first chamber or the second chamber based on the blockade current carried through the nanopore when the read voltage is applied.

15. The biomolecule measuring apparatus according to claim 14,
wherein: a plurality of the second chambers is provided such that the second chambers are isolated by a wall on one side of the chip;
the second electrode is individually disposed in the plurality of the second chambers; and
a plurality of the phase monitors, a plurality of the control circuits, and a plurality of the information processors are individually provided for the plurality of second electrodes.

* * * * *